United States Patent [19]
Koga et al.

[11] Patent Number: 6,146,893
[45] Date of Patent: Nov. 14, 2000

[54] METHOD OF SCREENING ELICITOR INDUCING THE PRODUCTION OF PHYTOALEXIN IN RICE AND RICE DISEASE CONTROLLING AGENT CONTAINING ELICITOR AS THE ACTIVE INGREDIENT

[75] Inventors: Jinichiro Koga, Saitama; Toyozo Yamauchi, Niigata; Kenji Umemura, Niigata; Michiaki Iwata, Niigata, all of Japan

[73] Assignee: Plant Biological Defense System Laboratories, Nishikanbara-gun, Japan

[21] Appl. No.: 09/147,418

[22] PCT Filed: Apr. 21, 1997

[86] PCT No.: PCT/JP97/01369

§ 371 Date: Dec. 21, 1998

§ 102(e) Date: Dec. 21, 1998

[87] PCT Pub. No.: WO98/47364

PCT Pub. Date: Oct. 29, 1998

[51] Int. Cl.[7] ...................................... C12N 5/00
[52] U.S. Cl. ...................... 435/410; 417/58.1; 504/116.1; 504/117
[58] Field of Search .............................. 435/410; 47/58.1; 504/116.1, 117

[56] References Cited

U.S. PATENT DOCUMENTS

| | | | |
|---|---|---|---|
| 5,240,951 | 8/1993 | Shimotori et al. | 514/372 |
| 5,602,111 | 2/1997 | Misaki et al. | 514/54 |
| 5,849,956 | 12/1998 | Koga, et al. | |

FOREIGN PATENT DOCUMENTS

| | | |
|---|---|---|
| 48-62936 | 9/1973 | Japan . |
| 60-190800 | 9/1985 | Japan . |
| 5-168490 | 7/1993 | Japan . |
| 7-43520 | 2/1995 | Japan . |
| 9-12504 | 1/1997 | Japan . |

OTHER PUBLICATIONS

S. Kumar, "Phytoalexins in Rice–Pyricularia oryzae Interaction: Factors Affecting Phytoalexin Production", (1993), vol. 28, No. 1, pp. 59–69.

N. T. Keen, "Specific Elicitors of Plant Phytoalexin Production: Determinants of Race Specificity in Pathogens?", Jan. 10, (1975), Science, vol. 187, pp. 74–75.

Janice K. Sharp, et al. "The Primary Structures of One Elicitor–active and Seven Elicitor–inactive Hexa (β–D–glucopyranosyl)–D–glucitols Isolated from the Mycelial Walls of *Phytophthora megasperma* f. sp. glycinea", Sep. 25, (1984), vol. 259, No. 18, pp. 11321–11336.

I. A. M. Cruickshank, et al. "The Isolation And Partial Characterization of Monilicolin A, A Polypeptide With Phaseollin–Inducing Activity From *Monilinia Fructicola*", Feb. 13, (1968), Life Sciences, vol. 7, Part II, No. 10, pp. 449–458.

R. M. Bostock, et al., Eicosapentaenoic and Arachidonic Acids from Phytophthora infestans Elicit Fungitoxic Sesquiterpenes in the Potato, Apr. 3, (1981), Science, vol. 212, pp. 67–69.

R. D. Sitrin, et al., "Isolation and Structure Determination of Pachybasium Cerebrosides Which Potentiate The Antifungal Activity of Aculeacin", (1987), Journel of Antibiotics, vol. XLI, No. 4, pp. 469–480.

Genshiro Kawai, et al., "Fruiting of *Schizophyllum commune* Induced by Certain Ceramides and Cerebrosides from *Penicillium funiculosum*", (1985),Agric. Biol. Chem.,49, pp. 2137–2146.

Genshiro Kawai, et al. "Structure of biologically active and inactive cerebrosides prepared from *Schizophyllum commune*", Journal of Lipid Research, vol. 26, (1985), pp. 338–343.

*Primary Examiner*—Leon B. Lankford, Jr.
*Attorney, Agent, or Firm*—Oblon, Spivak McClelland, Maier & Nuedtadt, P.C.

[57] ABSTRACT

An object of the present invention is to provide a method for screening elicitors that induce the production of phytoalexins in rice plants, and agents for controlling rice diseases; and relates to a method for screening elicitors that induce the production of phytoalexins in rice plants, wherein the aforementioned elicitor screening method is characterized by using rice seedlings as the test plant, applying a test sample on a suitable part of the rice seedlings, and then screening the elicitors using the phytoalexins produced in the plant bodies as marker substances, as well as to agents for controlling rice diseases containing as an active ingredient a specific compound having an action in inducing the production of phytoalexins in rice plants.

5 Claims, 9 Drawing Sheets

METHOD OF SCREENING ELICITOR INDUCING THE PRODUCTION OF PHYTOALEXIN IN RICE AND RICE DISEASE CONTROLLING AGENT CONTAINING ELICITOR AS THE ACTIVE INGREDIENT

TECHNICAL FIELD

The present invention relates to a method for screening elicitors that have the property of inducing the production of phytoalexins in rice plants, as well as to an agents for controlling rice diseases, which contain as an active ingredient an elicitor which has been screened by the said screening method. More particularly, the present invention relates to a method for rapidly and accurately screening elicitors that induce the production of phytoalexins in rice plants, characterized in that rice plants are cultivated for tests, a test sample is applied to a suitable part of the rice plants, and specific phytoalexins synthesized in the rice plant bodies are used as screening marker substances, so as to screen substances having the property of inducing the production of phytoalexins such as phytocassanes and momilactones and the like in rice plants. Because such phytoalexins have potent antimicrobial activity against causal organisms of rice plant diseases such as rice blast fungus (*Magnaporthe grisea*, previously designated as *Pyricularia oryzae*), rice sheath blight fungus (*Rhizoctonia solani*), and rice brown spot fungus (*Cochliobolus miyabeanus*), elicitors having the property of inducing the production of phytoalexins in rice plants would be useful as active ingredients in agents for controlling rice diseases.

The present invention also relates to the cerebroside compounds PO8, PO9, R2 and derivatives thereof which have action in inducing the production of phytoalexins in rice plants, and also relates to a method for using one or more of these substances as an agent to control rice diseases, as well as to a method for applying cerebroside compounds and derivatives to the leaves of rice plants so as to induce the production of the phytocassane and momilactone as phytoalexins in rice plants. Because such phytoalexins have potent antimicrobial activity against rice plant diseases such as rice blast, rice sheath blight, and rice brown spot, these cerebroside compounds and derivatives are useful as active ingredients in agents for controlling rice diseases.

BACKGROUND ART

Plants generally exhibit an antibiotic reaction (hypersensitive reaction) when they come into contact with a pathogenic fungi, and are known to produce phytoalexins having antifungal activity against the pathogenic fungus in the tissue around the reaction site. Examples of phytoalexins include momilactones A and B, oryzalexins A, B, C, D, E, F, and S, sakuranetin, oryzalic acids A and B, oryzalides A and B, and phytocassanes A, B, C, and D (Japanese Patent Application No. 7-43520/1995) discovered by the present inventors.

Substances that induce phytoalexin production in plant bodies are referred to as elicitors (N. T. Keen, Science 187: 74–75 (1975)), most of which have thus far been isolated from plant pathogenic fungi. Typical elicitors include hepta-β-D-glucopyranoside as polysaccharide isolated from *Phytophthora megasperma f.* sp. glycinea (J. K. Sharp, B. Valentand, P. Albersheim, J. Biol. Chem. 259: 11321–11336 (1984)), monicholine A as protein substance isolated from *Monilinia fructicola* (I. A. M. Cruickshank and D. R. Perrin, Life Sci. 7: 449–458 (1968)), and eicosapentaenoic acid as lipid isolated from Phytophthora infestans (R. M. Bostock, J. Kuc, and R. A. Laine, Science 212: 67–69 (1975)).

Since, as noted above, elicitors have action in inducing the production of phytoalexins in plant bodies that have antifungal activity against pathogenic fungi, they are considered substances which could serve as active ingredients in highly safe agents for controlling plant diseases based on an action different than that of conventional agrochemicals, and there has been a strong need for the discovery of useful elicitors and for novel screening methods that would allow substances having elicitor activity to be rapidly and easily screened as methods for discovering such useful elicitors.

Under these circumstances, the inventors undertook extensive and painstaking research in view of the aforementioned prior art to develop a novel screening method for screening useful elicitors that induce phytoalexin production in rice plants, but it is extremely difficult to screen for substances having elicitor activity using rice plant bodies, so much so that no effective methods have yet been established. In their various studies to develop an effective method, the inventors have succeeded in establishing a new basic technique relating to the species of test rice plants, rice cultivating methods, methods for applying test samples, phytoalexin analyses, and the like, and thus have discovered that substances having elicitor activity can be screened.

That is, as a result of their studies on rice used in tests, they have found that the matters relating to the variety and species of test rice plants, the cultivation temperature and humidity, the age of the test rice plants, the site where the test sample is applied, and the like are extremely important, and they have found that various optimal conditions of the matters can be established for using the same as a screening method. They also have determined a method for extracting phytoalexins induced in rice plant bodies and for analyzing them by HPLC, using phytocassanes and momilactones as preferred examples of phytoalexins.

Tests of various substances by the aforementioned method have revealed a number of compounds having elicitor activity.

The inventors attempted to screen substances having elicitor activity from microbial products by using the aforementioned screening method, and thus have discovered the substances having such elicitor activity widely existing in filamentous fungi, including plant pathogenic fungi.

Further, they also isolated such substances by means of solvent extraction, column chromatography, or the like, to obtain three types of resulting active substances, and structurally analyzed them and thereby they ascertained that the substances were the cerebroside compounds PO8, PO9, and R2 having the following structural formulas, and that these substances were effective as active ingredients in agents for controlling diseases in rice plants, and they have accomplished the present invention.

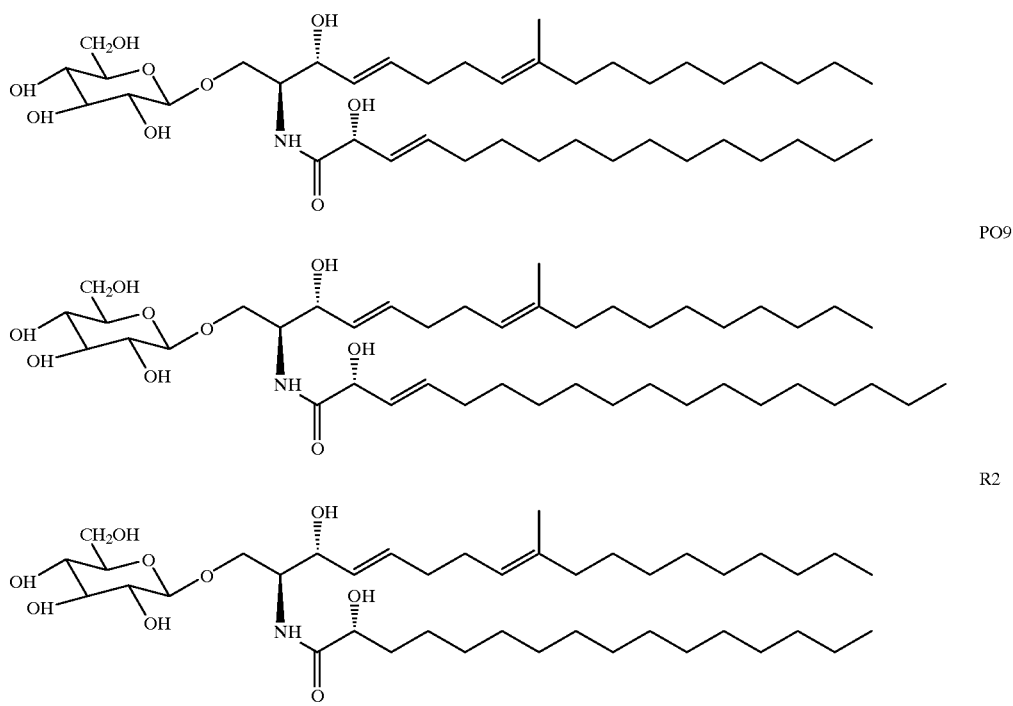

The chemical structures of the cerebroside compounds PO8, PO9, and R2 which discovered by them as substances having elicitor activity have already reported in references. PO8 has the same structure as cerebroside A (R. D. Sitrin et al, J. Antibiot. 41, 469–480 (1988)), PO9 has the same structure as PENII (G. Kawai et al, Agric. Biol. Chem. 49, 2137–2146 (1985)), and R2 has the same structure as cerebroside B (G. Kawai et al, J. Lipid. Res. 26, 338–343 (1985)). The substances having the elicitor activity related to the present invention, however, have not been described in the references and the inventors have firstly ascertained that these cerebroside compounds have activity in controlling diseases in rice plants.

SUMMARY OF THE INVENTION

An object of the present invention is to provide a method for screening elicitors that induce phytoalexin production in rice plants, and an agent for controlling rice diseases.

The present invention relates to a method for screening elicitors that induce the production of phytoalexins in rice plants, which comprises using rice seedlings as the test plant, applying a test sample on a suitable part of the rice seedlings, and them screening the elicitors using the phytoalexins produced in the plant bodies, as well as to agents for controlling rice diseases containing as an active ingredient a specific compound having an action in inducing the production of phytoalexins in rice plants.

The present invention is capable of simple and highly accurate screening of elicitors that induce phytoalexin production in rice plants, and can provide non-toxic, non-polluting rice plant disease control agents with low residual toxicity.

DISCLOSURE OF THE INVENTION

As described above, the present invention relates to a method for screening elicitors that induce phytoalexin production in rice plants, and also relates to a method in which phytoalexins (such as phytocassanes and momilactones and the like) that are produced in rice plant bodies are analyzed by HPLC. It also relates to substances with elicitor activity that are obtained by such a method.

That is, an object of the present invention is to provide a method for screening elicitors that induce phytoalexin production in rice plants.

Another object of the present invention is to provide a screening method for rapidly and accurately screening elicitors that have the property of inducing phytoalexin production in rice plants, using phytocassane and momilactone A as rice plants phytoalexins as marker substances.

Another object of the present invention is to provide agents for controlling rice plant diseases, which contain as an active ingredient a specific substance having an action in inducing phytoalexin production in rice plants.

The present invention to resolve the aforementioned objects relates to a method for screening elicitors that induce phytoalexin production in rice plants, which is characterized in that rice seedlings are used as the test plant, a test sample is applied on a suitable part of the rice seedlings, and the elicitors are screened using specific phytoalexins produced in the plant bodies as marker substances.

A preferred embodiment of the present invention is the above method for screening the elicitors, wherein a test sample is applied in the form of drops on the tips of the laminae of a rice seedling, and the phytoalexins produced in the plant bodies are extracted with solvent and analyzed by high performance liquid chromatography (HPLC) using phytocassanes and/or momilactone A as the rice plant phytoalexins as marker substances.

The present invention also relates to agents for controlling rice plant diseases, containing as an active ingredient one or more substances selected from 2-pyrazinecarboxylic acid, picolinic acid, 2,6-pyridinedicarboxylic acid, 2,3-pyridinedicarboxylic acid, pyrrole-2-carboxylic acid, oxonic acid, and cerebroside compounds PO8, PO9, and R2 and derivatives thereof, which are screened by the aforementioned screening method, having an action in inducing the production of phytoalexins in rice plants.

The present invention is described in further detail below.

The inventors undertook detailed study on varieties of test rice plants, cultivating conditions, conditions of phytoalexin analysis, and the like, as a method for screening substances that induce phytoalexin production in rice plants. They have found that "Akitakomachi," "Koshihikari," and the like were suitable varieties of rice plants for use in the tests, and that granular cultivation soils, specifically, HONENS cultivation soil No. 1 (National Federation of Agricultural Co-operative Associations), containing nitrogen, phosphates, and potassium fertilizer, which are necessary for the growth of rice plants, were suitable cultivating soils, and that it was important to control temperature, humidity, and light as conditions for cultivating the test rice plants. Particularly, germinated seeds, for example, are planted in pots, are cultivated for about 2 to 3 days in a dark room at 30 to 32° C., and are transferred to an artificial weather room when the sprouts have grown about 2 to 3 cm above the soil. The artificial weather room is maintained at a temperature of 18 to 20° C., a humidity of 80 to 85%, and an illuminance of 2000 to 3000 lux. At the stage of second main leaves are developed, the conditions in the room are changed to an illuminance of 3000 to 4000 lux, a humidity of 95 to 100%, and a daytime temperature of 27 to 30° C., and the plants are cultivated until the fifth main leaves are fully developed. These cultivation conditions can, of course, be suitably modified within the ranges given above. Test samples are preferably applied in the form of drops using a capillary pipet on the tips of the laminae of fifth main leaves.

Rice plants to which the test samples have been applied are grown for another week, and the leaves on which the test samples have been applied are cut to pieces for extraction with a solvent such as ethyl acetate, methanol, and the like. The extract is analyzed by HPLC, and for example, with respect to phytocassanes and momilactone, the amount of the phytoalexins which have been induced can be determined from the peak heights of phytocasane A at a retention time of around 35 minutes, phytocasane B at a retention time of around 43 minutes, and momilactone A at a retention time of around 50 minutes. Other phytoalexins can be similarly analyzed. The aforementioned screening method essentially comprises the following constitutions.

(1) Test Plants (Rice Plants)
  ((1)) Variety: Akitakomachi and Koshihikari
  ((2)) Age: Rice seedlings, particularly with fifth main leaves
  ((3)) Cultivation: Cultivated until sixth main leaves are fully developed
(2) Application of Test Samples
  ((1)) Application site: lamina of the test plants, particularly the tip thereof
  ((2)) Method of application: test samples are applied in the form of drops using capillary pipet and the like
  ((3)) Cultivation period after application: about 1 week
(3) Extraction and Analysis
  ((1)) Preparation of samples: laminae treated with the test samples are cut into pieces
  ((2)) Extraction: samples are extracted with solvent such as ethyl acetate and methanol and the like
  ((3)) Analysis: HPLC analysis According to this screening method, the compounds given in Example 2 below and the like were detected as substances that induced phytoalexin production in rice plants.

In the course of various experiments assaying the amount of phytoalexins produced in rice plant bodies following the application of samples to the surface of rice plant laminae and a subsequent suitable period of cultivation in an effort to use the aforementioned screening method to screen substances that induce phytoalexin production, the inventors have confirmed that products extracted with organic solvents from filamentous fungal cells, including plant pathogens such as rice blast fungus and rice sheath blight fungus ant the like, showed high activity in inducing phytoalexins. Substances that induce phytoalexin production, such as PO8 and PO9, can be isolated in the form of single component respectively by extracting cells of rice blast fungus with a solvent such as ethyl acetate, acetone, or ethanol and the like, and by purifying the extract by means of HPLC, thin layer chromatography, or the like.

Examples of liquid media which can be used to culture the plant pathogens used in the present invention include any conventional medium used for the culture of fungi using plant or microbial extracts, although PSY medium and the like are preferred, for example. Plant extract components of potato or the like, or extract of yeast or the like, may be used as such media.

Desirable examples of specific processes for the extraction and separation of PO8 and PO9 include, but are not limited to, those in which cells of rice blast fungus are extracted with a solvent such as ethyl acetate and the like, and the extracts are fractionated by HPLC using a column such as TSK gel ODS 120A or ODS 120T (by Tosoh), purified and isolated by a purification process such as concentration to dryness and the like.

Other similar purification means can be used in suitable combinations. The purification process is not particularly limited. R2 can also be purified and isolated from rice sheath blight fungus, for example, by similar purification means.

The PO8, PO9, and R2 relating to the present invention have the following characteristics.

1) Mass spectrometry by FAB-MS revealed a molecular weight of 725 for PO8, 753 for PO9, and 727 for R2.
2) PO8, PO9, and R2 showed the infrared absorption spectra given in FIGS. 1 through 3.
3) PO8, PO9, and R2 showed the $^1$H-NMR spectra given in FIGS. 4 through 6.
4) PO8, PO9, and R2 showed the $^{13}$C-NMR spectra given in FIGS. 7 through 9.
5) PO8, PO9, and R2 have an action in inducing phytoalexin production in rice plants. Examples of phytoalexins that are induced include phytocassanes A, B, C and D, and momilactones A and B and the like. Since these phytoalexins have potent antifungal activity against rice blast fungus, rice sheath blight fungus, and rice brown spot fungus, it is assumed that rice plants in which such substances have been induced would show resistance against infection by these pathogens.

As shown in the examples below, the PO8, PO9, and R2 relating to the present invention have the property of inducing antimicrobial phytoalexin production in rice plants, and are thus useful as active ingredients in agents for controlling diseases in rice plants such as rice blast, rice sheath blight, and rice brown spot. That is, the application of these compounds in the form of suitable preparations to rice plants can prevent the rice plants from being infected with these diseases.

As shown in the examples below, the agents for controlling rice plant diseases in the present invention should be prepared in suitable formulations which contain the aforementioned active ingredients in suitable amounts, depending on the purpose for which they are being used. The configuration, preparation means, and the like are not particularly limited. As indicated in the examples below, desirable methods by which the compounds having an action in inducing phytoalexin production in rice plants are applied to rice plants include, but are not limited to, those in which the compound is dissolved in a 20 mM phosphate buffer (pH 7.0) containing 0.1% Tween 20, and the resulting solution is sprayed on rice plants. Other methods may be used, and no limitations are imposed on the configuration of the agents for applying the compound to rice plants, the aspect in which it is used, the method of application, and the like.

BEST MODE FOR CARRYING OUT THE INVENTION

Figure 1:
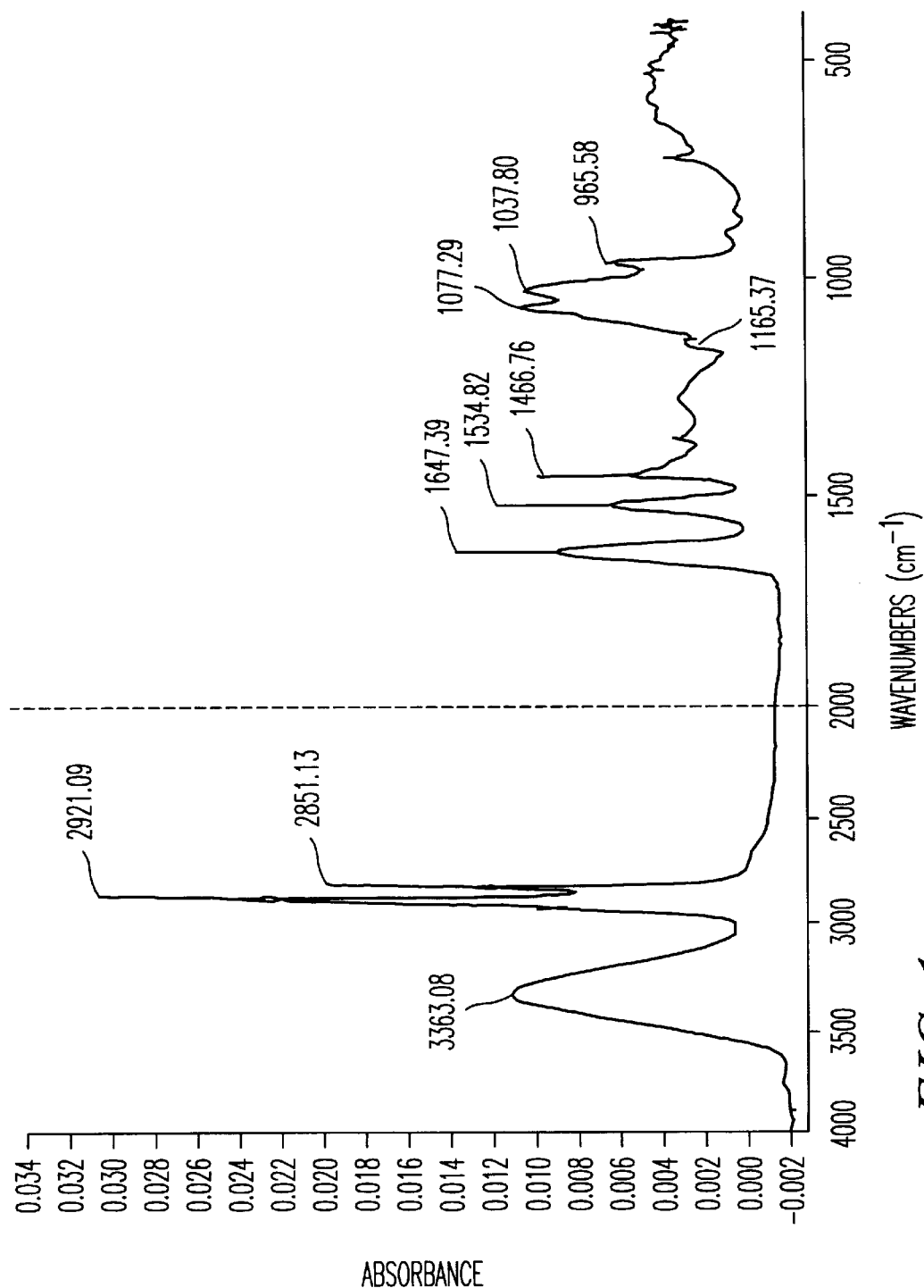
FIG. 1 depicts the infrared absorption spectrum for the cerebroside compound PO8 relating to the present invention.
Figure 2:
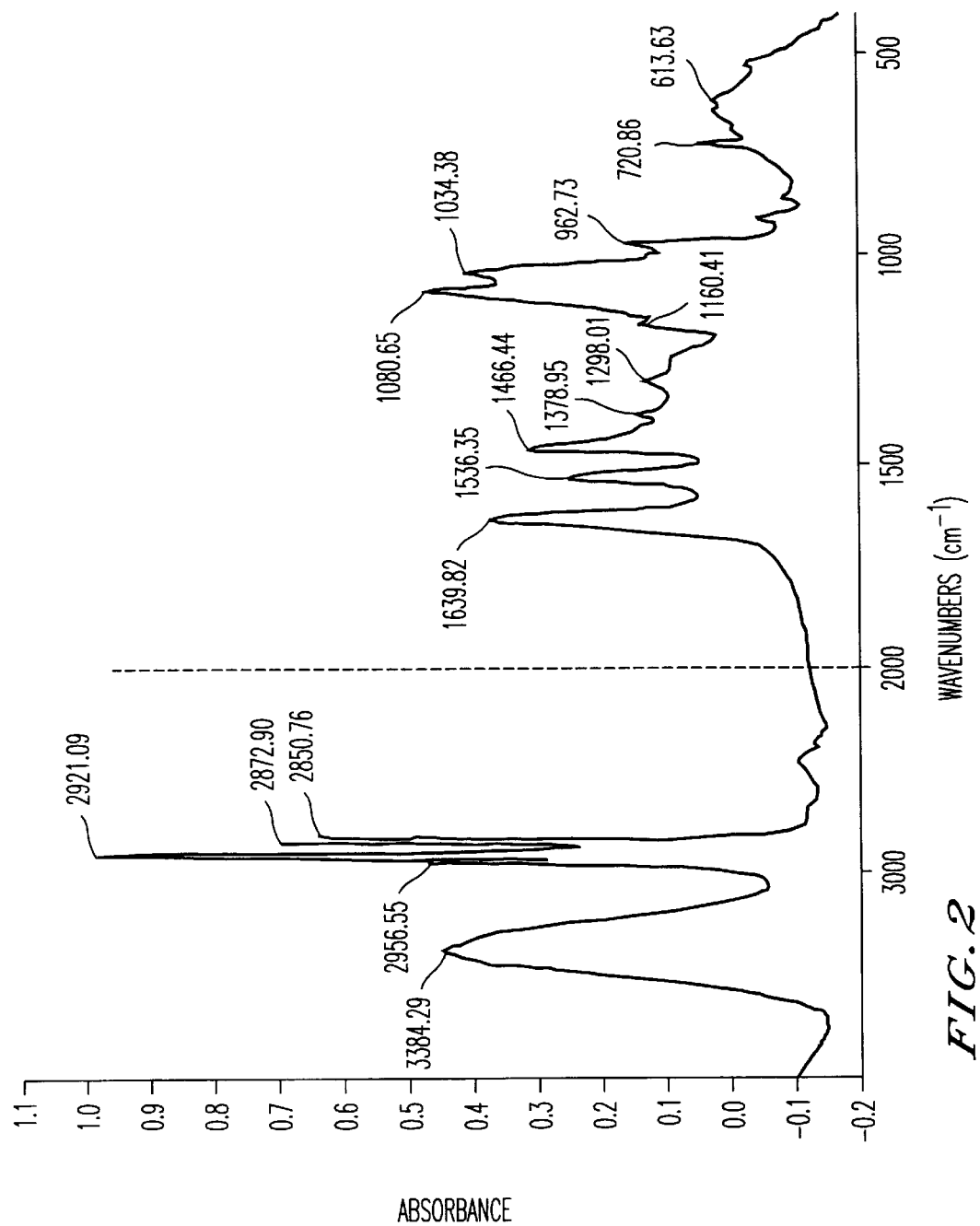
FIG. 2 depicts the infrared absorption spectrum for the cerebroside compound PO9 relating to the present invention.
Figure 3:
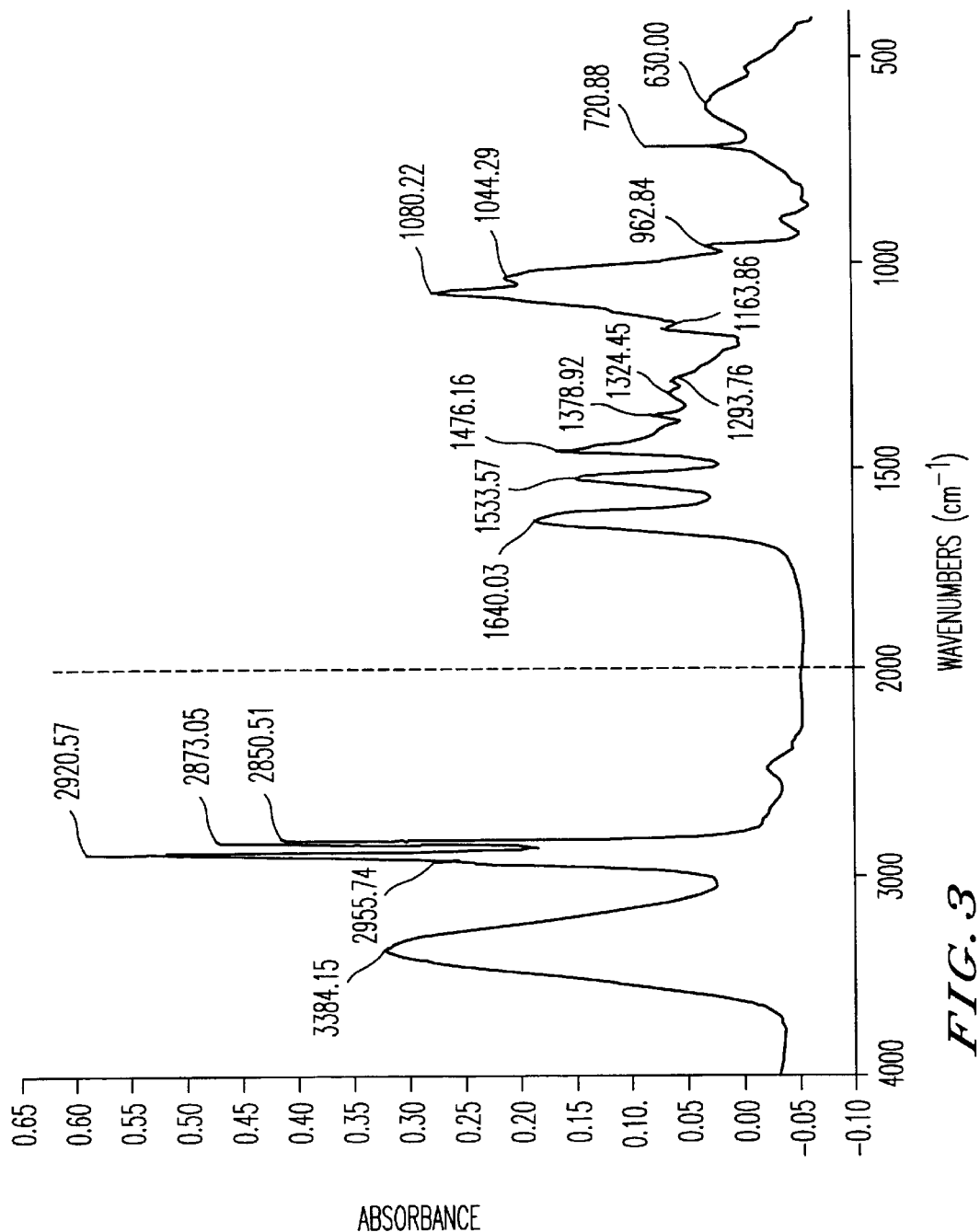
FIG. 3 depicts the infrared absorption spectrum for the cerebroside compound R2 relating to the present invention.
Figure 4:
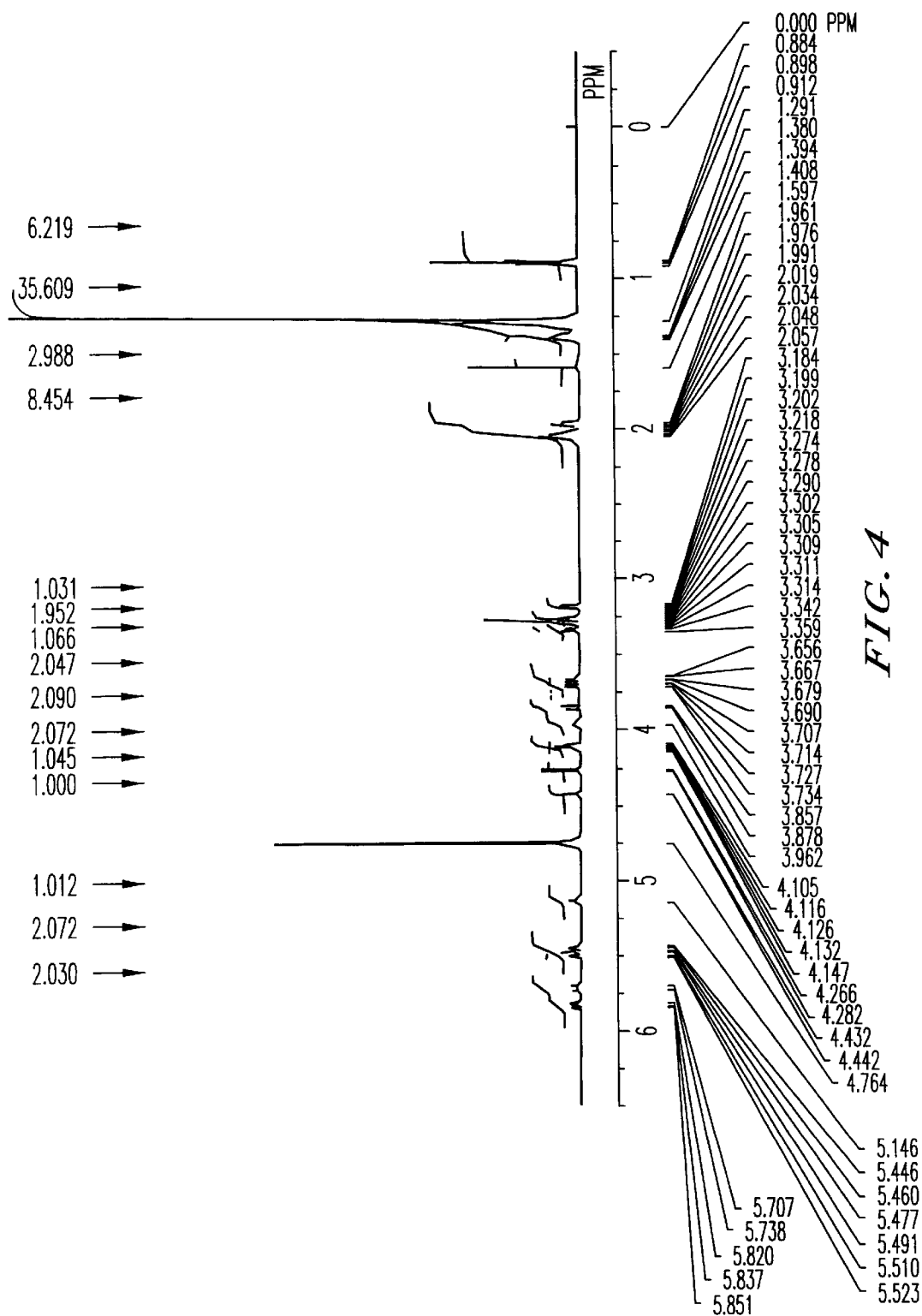
FIG. 4 depicts the $^1$H-NMR spectrum for the cerebroside compound PO8 relating to the present invention.
Figure 5:
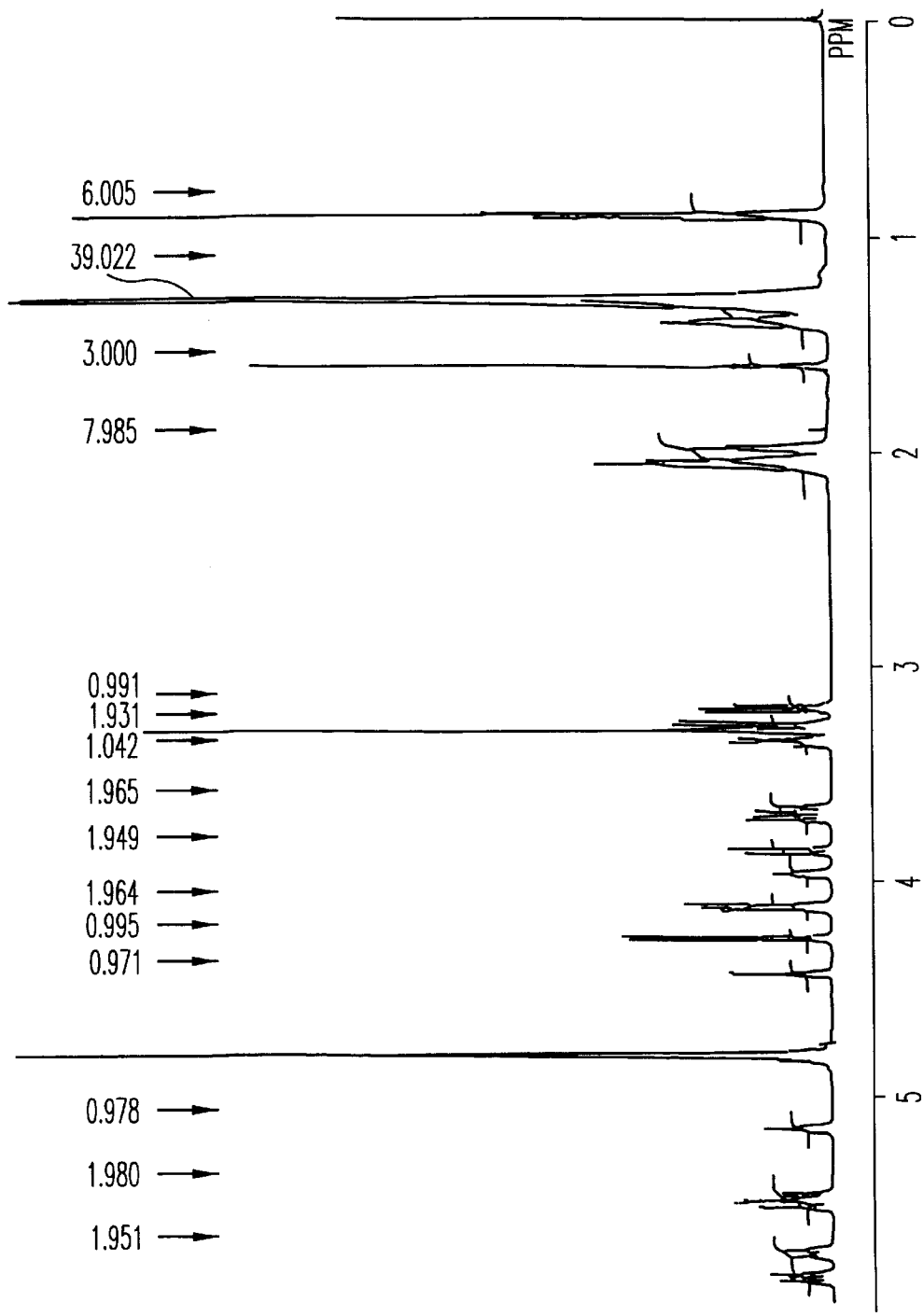
FIG. 5 depicts the $^1$H-NMR spectrum for the cerebroside compound PO9 relating to the present invention.
Figure 6:
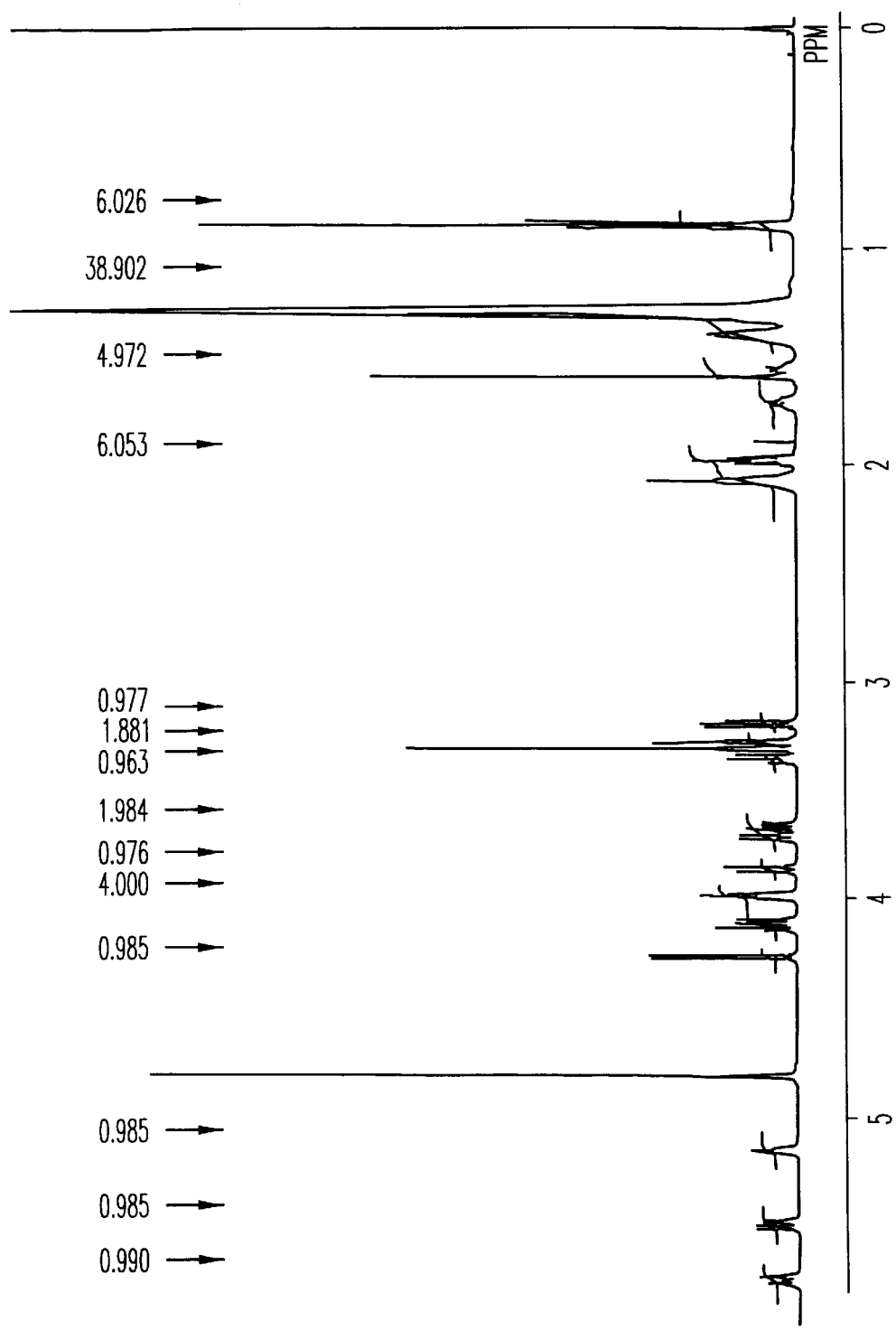
FIG. 6 depicts the $^1$H-NMR spectrum for the cerebroside compound R2 relating to the present invention.
Figure 7:
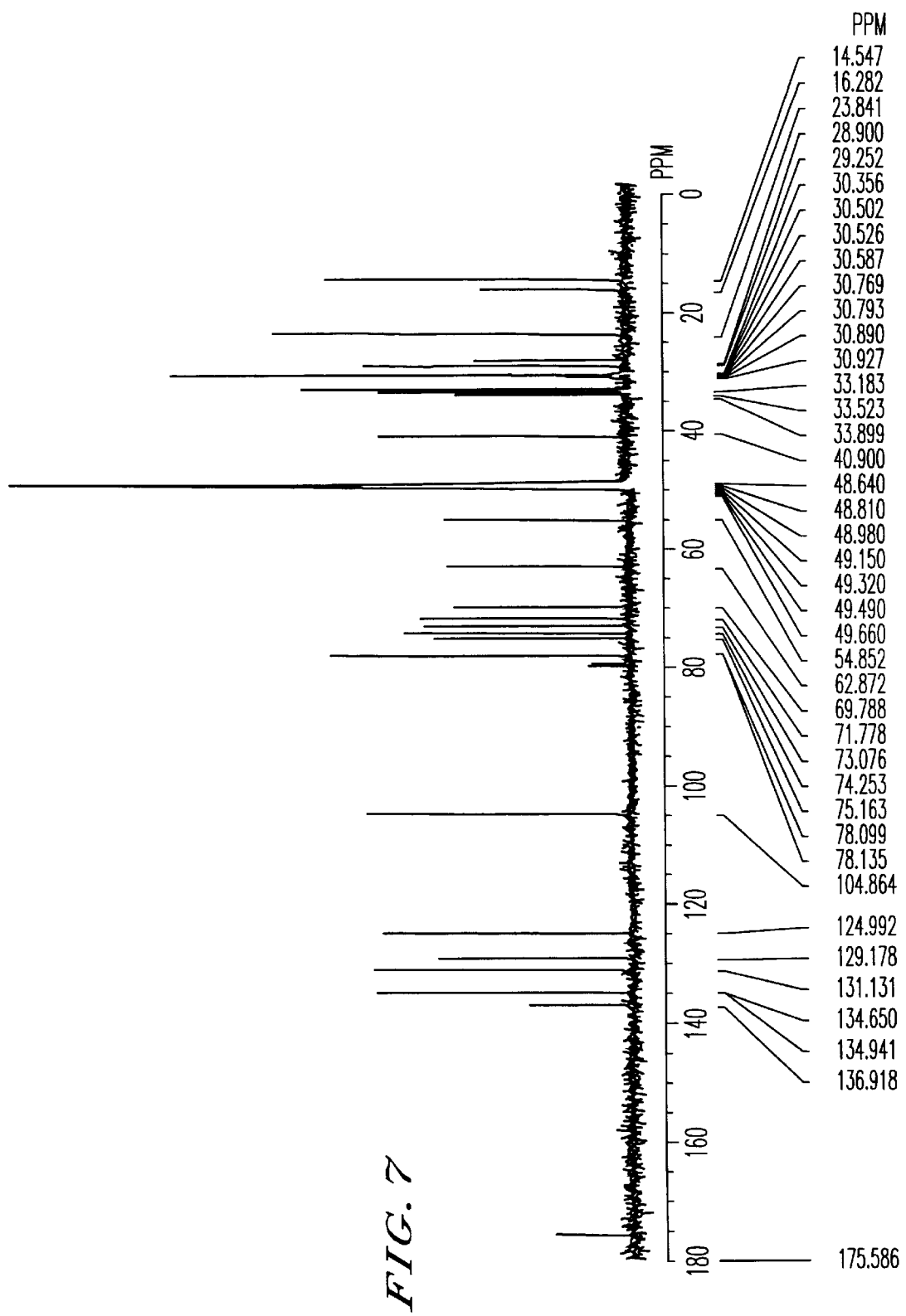
FIG. 7 depicts the $^{13}$C-NMR spectrum for the cerebroside compound PO8 relating to the present invention.
Figure 8:
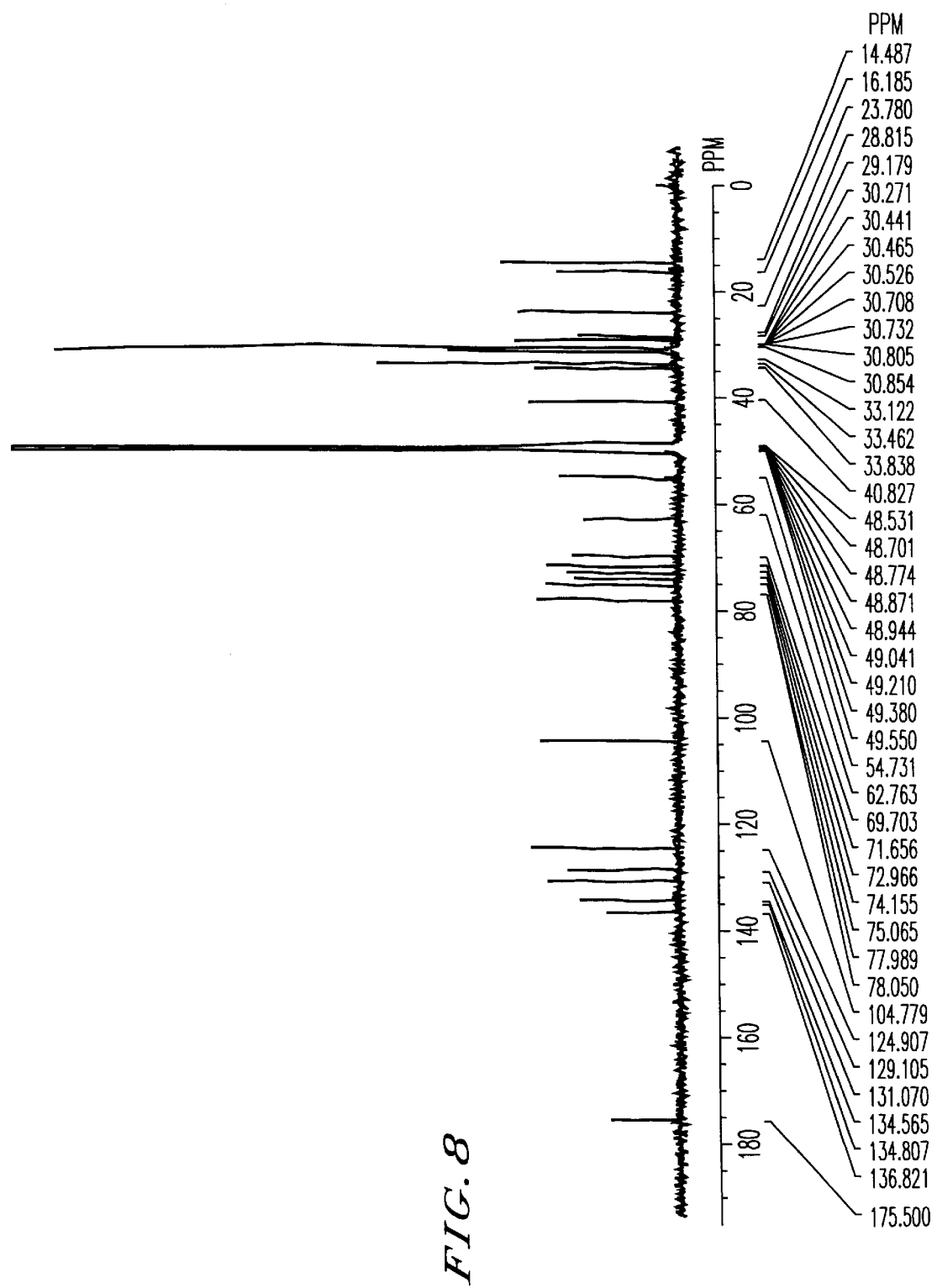
FIG. 8 depicts the $^{13}$C-NMR spectrum for the cerebroside compound PO9 relating to the present invention.
Figure 9:
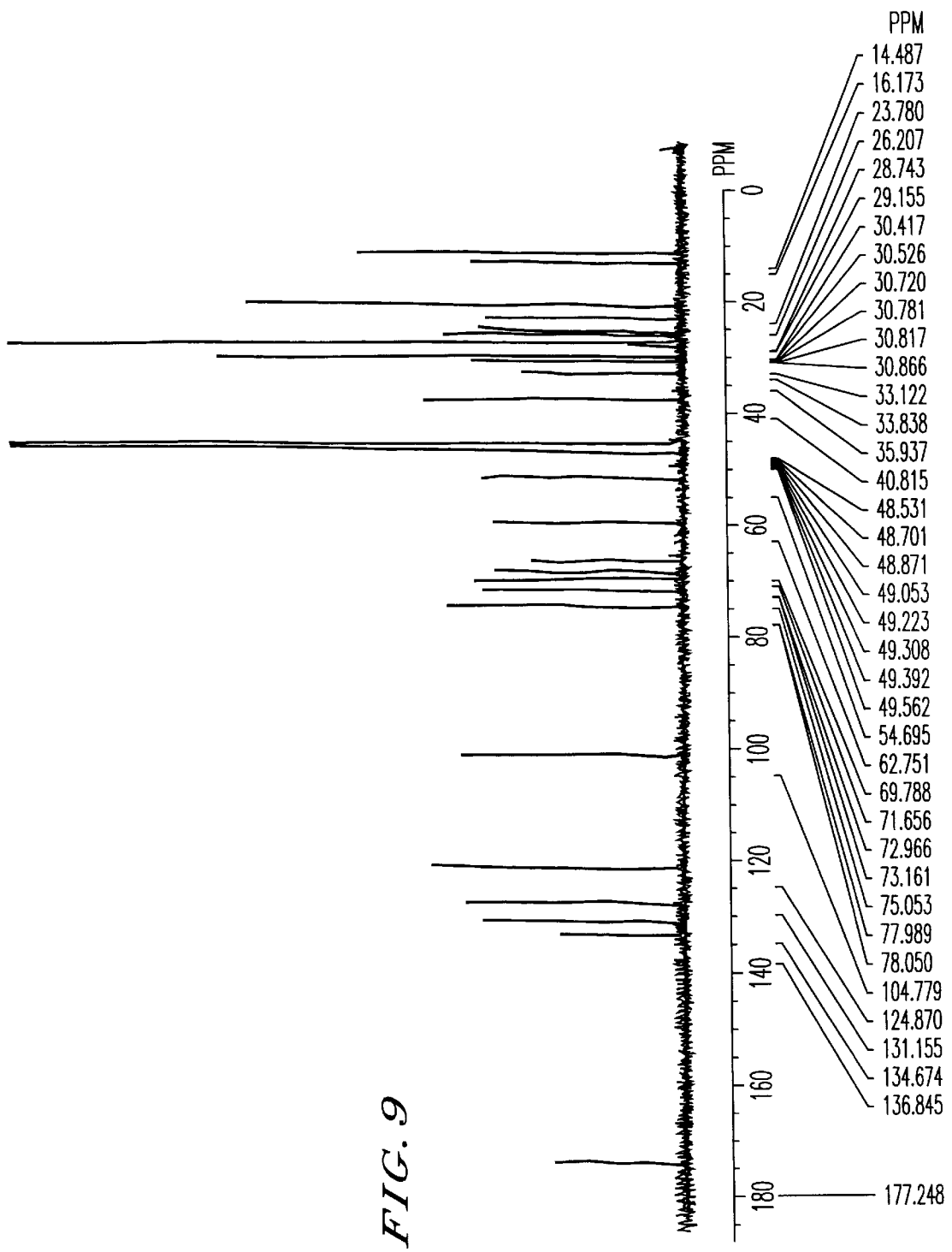
FIG. 9 depicts the $^{13}$C-NMR spectrum for the cerebroside compound R2 relating to the present invention.

The present invention is described in detail below with reference to examples, but the present invention is not limited in any way by the following examples.

EXAMPLE 1

(1) Cultivation of Rice Plants Used As Test Plants

Rice plant seeds (varieties: Akitakomachi or Koshihikari) were allowed to germinate after being sorted in saline to remove defective seeds. Eight germinated seeds were planted in pots with a diameter of 6 cm filled with HONENS cultivation soil No. 1 (National Federation of Agricultural Co-operative Associations), and they were grown for about 2 to 3 days in a 32° C. dark room. When the sprouts had grown about 2 to 3 cm above ground, they were transferred to glass cases in an artificial whether room. The artificial weather room was maintained at a temperature of 18° C., a humidity of 80%, and an illuminance of 2000 lux, but the rice plant pots were placed in locations somewhat shielded from the light. At the stage of second main leaves were developed, the conditions were changed to an illuminance of 3000 plux, a humidity of 100%, and a daytime temperature of 27 to 30° C., and the plants were grown until the fifth main leaves were fully developed.

Rice plants seedlings which had thus been cultivated were used in the following tests.

(2) Application of Samples, and Induction of Phytoalexins

Samples 1 through 6 were prepared as indicated in Table 1.

20 μL each of sample solution was applied using a capillary pipet in ten spots at the tips of the laminae of fifth main leaves of rice plant seedlings cultivated as described above. The samples were dissolved to the prescribed concentration in 20 mM phosphate buffer (pH 7.0) containing 0.1% Tween 20 for use in tests to induce phytoalexins.

Rice plants to which the samples had been applied were grown for 3 days in an artificial weather room with a humidity of 80%, an illuminance of 2000 lux, a night time temperature of 18° C., and a day time temperature of 23° C. The day time humidity was adjusted to 100%, and the plants were grown another 4 days.

(3) Phytoalexin Extraction and Analysis

Eight rice plant laminae to which samples had been applied were cut to pieces, and 10 mL of a mixture of ethyl acetate and 0.1 N $Na_2CO_3$ (1:1) was added thereto and the laminae were extracted under shaking over night. The extract was separated by centrifugation (5000 rpm, 4° C., 20 min), the supernatant (ethyl acetate phase) was partitioned, and concentrated to dryness. The dry extract was dissolved in 0.4 mL ethanol, and 0.6 mL of 0.02 N HCl was added thereto and then the extract was mixed. This mixture was centrifuged, and 100 μL of the resulting supernatant was analyzed by HPLC. The HPLC conditions are given below.

Column: TSK-gel ODS 120T (4.6 mm×300 mm)

Solvent: acetonitrile-water (45:55) (volumetric ratio)

Flow rate: 1.2 mL/min

Temperature: 50° C.

Detector: UV 280 nm (phytocassane)/215 nm (momilactone)

(4) Results

As the results of screening of a wide range of compounds by the aforementioned method, it has been revealed that the following samples 1 through 6 had an action in inducing phytoalexin production in the rice plants.

1) 2-pyrazinecarboxylic acid
2) picolinic acid
3) 2,6-pyridinedicarboxylic acid
4) 2,3-pyridinedicarboxylic acid
5) pyrrole-2-carboxylic acid
6) oxonic acid, potassium salt 1. 2-Pyrazinecarboxylic acid

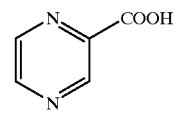

2. Picolinic acid

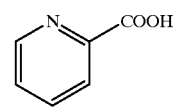

3. 2,6-Pyridinedicarboxylic acid

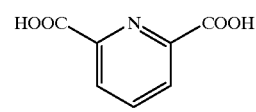

4. 2,3-Pyridinedicarboxylic acid

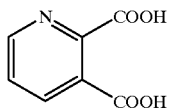

5. Pyrrole-2-carboxylic acid

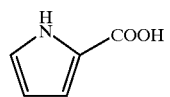

6. Oxonic acid, potassium salt

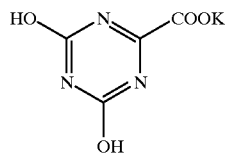

EXAMPLE 2

TABLE 1

| | | Amount of phytoalexins induced | | |
|---|---|---|---|---|
| | Sample | Amount of phytoalexins (μg/g leaves) | | |
| Sample No. | Concentration (%) | Phytocassane A | Phytocassane B | Momilactone A |
| 1 | 0.1 | 1.3 | 5.6 | 5.7 |
| 2 | " | 4.9 | 10.5 | 7.8 |
| 3 | " | 2.6 | 9.8 | 11.7 |
| 4 | " | 2.6 | 8.0 | 13.3 |
| 5 | " | 3.1 | 5.7 | 11.7 |
| 6 | " | 20.2 | 28.9 | 18.8 |

Table 1 demonstrates that Samples 1 through 6 have an action in inducing phytoalexin production in the rice plants, and it has been revealed that they are useful as active ingredients in agents for controlling rice diseases.

EXAMPLE 3

Manufacture of PO8 and PO9
(1) Culture of Rice Blast Pathogens
200 g of peeled potatoes were cut to pieces, 1 L of distilled water was added thereto, and the material was autoclaved for 60 minutes at 121° C. Following the autoclaving, the solids were filtered off with gauze to prepare 1 L filtrate. 2% saccharose and 0.5% yeast extract were added to the filtrate to prepare PSY medium. Each 200 mL of the medium was transferred to 500 mL Erlenmeyer flask respectively, sterilized for 40 minutes at 121° C., and cooled. The medium was inoculated with rice blast pathogens (race 031 strain), and was subjected to shake culture (150 rpm) for 7 days at 26° C.
(2) Extraction and Purification of PO8 and PO9
Following the completion of the culture, the cultured product was filtered with gauze to separate the rice blast pathogen cells. Distilled water was added to the cells in an amount approximately 5-fold that of the cell weight, and the pH of them was adjusted to 10.5, and then the cells were extracted under stirring with ethyl acetate added thereto in a volume equal to that of the water. The ethyl acetate phase was portioned, and distilled in vacuo to remove the ethyl acetate and to obtain an oily residue. The residue was dissolved in 85% ethanol, and the resulting sample was introduced into a TSK gel ODS 120A HPLC column (21.5 mm×375 mm, Tosoh) and eluted with 91% ethanol (10 mL/min). PO8 was eluted at a retention time of around 25 minutes, while PO9 was eluted at a retention time of around 30 minutes. The fractions were collected, and subjected again to the same column chromatography. The PO8 was eluted at a retention time of around 60 minutes with 81% ethanol (10 mL/min), while the PO9 was eluted at a retention time of around 40 minutes with 86% ethanol (10 mL/min). Further, the fractions were collected, and subjected to HPLC using a TSK gel ODS 120T column (21.5 mm×375 mm, Tosoh), and fractionated with 95% acetonitrile (10 mL/min) to elute PO8 at a retention time of around 43 minutes and PO9 at a retention time of around 60 minutes. The fractions were collected, and distilled to remove solvent and to obtain PO8 and PO9 in the form of pure products.

EXAMPLE 4

Preparation of R2
Following the culture and crude extraction with ethyl acetate of rice sheath blight pathogens under the same conditions as those for the rice blast pathogens, the collected fractions were subjected to HPLC. The fractions were introduced into a TSK gel ODS 120A column (21.5×375 mm, Tosoh) in the primary purification by the HPLC to elute R2 at a retention time of around 26 minutes with 91% ethanol (10 mL/min).
Further, the fractions were purified by the chromatography with 86% ethanol (10 mL/min) in secondary purification to elute R2 at a retention time of around 50 minutes. The obtained fractions were further subjected to a TSK gel ODS 120T column (21.5 mm×375 mm, Tosoh) at a flow rate of 10 mL/min with a mixture containing 46.5% each of acetonitrile and ethanol to elute and to obtain completely purified R2 at a retention time of about 53 minutes.

EXAMPLE 5

Phytoalexin Induction With PO8, PO9, and R2
(1) Phytoalexin Production
The PO8, PO9, and R2 obtained in Example 1 were dissolved in a 20 mM phosphate buffer (pH 6.5) containing 0.1% Tween 20 to prepare 100 ppm sample solutions. The sample solutions with these concentrations and solvent solutions containing no samples were applied to rice plants (variety: Akitakomachi) cultivated in pots, and the activity in inducing phytoalexin production was assayed. In this case, the location where samples were applied was the tip of the lamina of fully developed fifth main leaves, and 20 μL (per leaf) of each sample solution was applied in the form of drops using a capillary pipet to ten locations at suitable intervals.
(2) Extraction of Phytoalexins
Rice plants treated with the sample solutions were cultivated for 7 days in an artificial weather room, eight treated leaves were then taken and cut to pieces, and the material was shaken in 10 mL of a mixture of ethyl acetate and 0.1 N sodium carbonate (1:1, pH 10) added thereto over night. The ethyl acetate phase was portioned, concentrated to dryness, and then dissolved again in 4 mL ethanol.
(3) Analysis by HPLC 0.6 mL of 0.02 N HCl was added to and mixed with the solution, and the mixture was then centrifuged. 100 μL of the resulting supernatant was analyzed by HPLC.

The HPLC conditions are given below.

Column: TSK-gel ODS 120T (4.6 mm×300 mm, Tosoh)

Solvent: acetonitrile-water (45:55) (volumetric ratio)

Flow rate: 1.2 mL/min

Temperature: 50° C.

Detector: UV 280 nm (phytocassane)/215 nm (momilactone)

Table 2 below shows the amount of phytoalexins that were induced. Table 2 clearly shows that the PO8, PO9, and R2 relating to the present invention have activity in inducing high concentrations of phytoalexins (phytocassanes A and B, and momilactones A and B) in the rice plants.

TABLE 2

Amount of phytoalexins induced

| Sample | Sample Concentration (μg/mL) | Amount of phytoalexans (μg/g leaves) | | |
|---|---|---|---|---|
| No. | | Phyto-cassane A | Phyto-cassane B | Momilactones A + B |
| Control (buffer) | 0 | 0.4 | 1.1 | 4.0 |
| PO8 | 100 | 10.9 | 6.9 | 28.6 |
| PO9 | 100 | 7.7 | 5.2 | 22.8 |
| R2 | 100 | 11.8 | 7.3 | 32.7 |

EXAMPLE 6

Rice Blast disease Control Test (1) Method

Eight rice plant (variety: Akitakomachi) seeds were planted per pot and cultivated in an artificial weather room, and a sample was sprayed on the seedlings at the stage of third to fourth main leaves. PO8 was dissolved (50 μg/mL) in 20 mM phosphate buffer (pH 7.0) containing 0.1% Tween 20, and 2 mL of the sample per pot was sprayed on the seedlings, with 5 pots per section. Seedlings were sprayed with 20 mM phosphate buffer (pH 7.0) containing 0.1% Tween, and water as controls. The plants were allowed to stand for 2 hours at room temperature following the treatment to allow the surface of the leaves to dry, and they were then cultivated again in the artificial weather room. The surface of the seedlings was sprayed with a suspension of conidia of rice blast pathogen (race 007 strain: having affinity) three days following chemical treatment. They were then infected with the pathogen after being allowed to stand for 36 hours in a dark humid room. They were then transferred to an artificial weather room to continue cultivation, and infected lesions appeared on fourth main leaves in each section after 5 days were measured to assess the controlling effects.

(2) Results 21.8 lesions per leaf were found in section sprayed with just water, and 19.3 lesions per leaf were found in section sprayed with phosphate buffer containing no sample. In contrast, there were 2.7 lesions per leaf in the section sprayed with PO8, showing that PO8 was obviously effective in controlling diseases. With respect to separately tested PO9 and R2, the same effects were found.

EXAMPLE 7

Test Agent for Controlling Rice Brown Spot Disease (1) Method

The effects of PO9 in controlling rice brown spot were studied under the same conditions as in the controlling test against rice blast (cultivation of test plants, application of samples, and method of infection of pathogen). However, the number of lesions were counted to assess the effects two days after a suspension of conidia of the rice brown spot pathogen was sprayed.

(2) Results 51.3 lesions per leaf were found in the control section which had been sprayed with water, whereas 13.4 lesions per leaf were found in the section which had been sprayed with PO9 in a concentration of 25 μg/mL, and 10.8 lesions were found per leaf in section which had been sprayed with PO9 in a concentration of 50 μg/mL, clearly demonstrating the effects of PO9 in controlling diseases.

The above examples show that the cerebroside compounds PO8, PO9, and R2 relating to the present invention are useful as active ingredients in agents for controlling rice plant diseases.

EXAMPLE 8

Formulation Example 1

Liquid Formulation

The substance having elicitor action in the present invention and other components were blended in the following proportions to prepare a liquid formulation by a common method.

| | |
|---|---|
| PO8 | 0.25% |
| Tween 20 (Wako Junyaku) | 5% |
| 20 mM potassium phosphate buffer (pH 7.0) | 94.75% |

At the time of use thereof, the aforementioned liquid formulation is diluted 50 to 200-fold for spraying.

Formulation Example 2

Water Dispersible Powder

The substance having elicitor action in the present invention and other components were blended in the following proportions to prepare a water dispersible powder by a common method.

| | |
|---|---|
| PO9 | 5% |
| SORUPOLU 8070 (anionic surfactant: Toho Kagaku Kogyo) | 10% |
| NEW CALUGEN WG-2 (anionic surfactant: Takemoto Yushi) | 5% |
| Carboxymethylcellulose | 3% |
| Neutral anhydrous sodium sulfate | 16% |
| Clay | 61% |

At the time of use thereof, the aforementioned preparation is diluted 500 to 4000-fold for spraying.

Formulation Example 3

Powder

The substance having elicitor action in the present invention and other components were blended in the following proportions to prepare a powder by a common method.

| | |
|---|---|
| R2 | 3% |
| White carbon | 1% |
| Diisopropyl phosphate | 2% |
| Talc | 94% |

Formulation Example 4

Flowable Formulation

The substance having elicitor action in the present invention and other components were blended in the following proportions to prepare a flowable by a common method.

| | |
|---|---|
| PO8 | 5% |
| Polyethylene glycol | 10% |
| Xanthan gun | 0.4% |
| NEW CALUGEN FS-1 (nonionic surfactant: Takemoto Yushi) | 6% |
| NEW CALUGEN FS-4 (anionic surfactant: Takemoto Yushi) | 10% |
| Silicone | 0.2% |
| Water | 68.4% |

At the time of use thereof, the aforementioned preparation is diluted 500 to 4000-fold for spraying.

INDUSTRIAL APPLICABILITY

The present invention relates to a method for screening substances that induce phytoalexin production in rice plants, and to agents or the like for preventing rice plant diseases, which contain as an active ingredient a specific substance having an action in inducing phytoalexin production in rice plants.

The present invention has the following effects.

1) elicitors that induce phytoalexin production in rice plants can be readily and accurately screened.

2) methods and analyses are provided using phytocassanes and momilactone a of the rice phytoalexins as marker substances to screen elicitors that induce phytoalexin production in rice plants.

3) agents for controlling rice plant diseases containing as an active ingredient specific substances that have an action in inducing phytoalexin production in rice plants are provided.

4) phytoalexins have antimicrobial action against rice plant diseases such as rice blast, rice sheath blight, rice brown spot, and the like, and substances which have been screened by the screening method of the present invention are thus useful as active ingredients in agents for controlling rice plant diseases such as rice blast, rice sheath blight, and rice brown spot.

What is claimed is:

1. A method for screening for an elicitor that induces the production of phytoalexins in rice plants, comprising:

applying a test sample in the form of drops on the tips of the laminae of potted rice seedlings;

extracting the phytoalexin produced in the rice seedlings with a solvent, to produce an extract; and detecting the presence of phytocassanes and/or momilactone A in the extract by high performance liquid chromatography (HPLC).

2. A method of controlling rice plant diseases, comprising:

identifying an elicitor that induces the production of phytoalexins in rice plants according to the screening method of claim 1; and applying the elicitor to rice plants.

3. The method of claim 2, wherein the elicitor is selected from the group consisting of cerebroside compound PO8, cerebroside compound PO9, and cerebroside compound R2.

4. A method of controlling rice plant diseases, comprising applying to rice plants an effective amount of at least one elicitor identified by the screening method of claim 1.

5. The method of claim 4, wherein the elicitor is selected from the group consisting of cerebroside compound PO8, cerebroside compound PO9, and cerebroside compound R2.

* * * * *